(12) United States Patent
Mullick et al.

(10) Patent No.: US 10,238,368 B2
(45) Date of Patent: Mar. 26, 2019

(54) METHOD AND SYSTEM FOR LESION DETECTION IN ULTRASOUND IMAGES

(71) Applicant: General Electric Company, Schenectady, NY (US)

(72) Inventors: Rakesh Mullick, Bangalore (IN); Pavan Kumar Veerabhadra Annangi, Bangalore (IN); Xiaoxing Li, Cupertino, CA (US); Vidya Pundalik Kamath, Clifton Park, NY (US); Fei Zhao, Schenectady, NY (US); Vivek Prabhakar Vaidya, Bangalore (IN); Soma Biswas, Karnataka (IN)

(73) Assignee: General Electric Company, Schenectady, NY (US)

( * ) Notice: Subject to any disclaimer, the term of this patent is extended or adjusted under 35 U.S.C. 154(b) by 636 days.

(21) Appl. No.: 14/033,452

(22) Filed: Sep. 21, 2013

(65) Prior Publication Data

US 2015/0087982 A1     Mar. 26, 2015

(51) Int. Cl.
*A61B 8/08*     (2006.01)
*G06T 7/00*     (2017.01)
*G06T 7/41*     (2017.01)

(52) U.S. Cl.
CPC ............ *A61B 8/5223* (2013.01); *A61B 8/085* (2013.01); *G06T 7/0012* (2013.01); *G06T 7/41* (2017.01); *G06T 2207/10132* (2013.01); *G06T 2207/20076* (2013.01); *G06T 2207/30068* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 5,984,870 A | 11/1999 | Al-Hallaq et al. | |
| 6,317,617 B1 | 11/2001 | Gilhuijs et al. | |
| 7,298,883 B2 | 11/2007 | Bonta et al. | |
| 7,466,848 B2 * | 12/2008 | Metaxas ................. | A61B 5/055 382/128 |
| 7,640,051 B2 | 12/2009 | Krishnan et al. | |

(Continued)

OTHER PUBLICATIONS

Nanni et al. "Local binary patterns variants as texture descriptors for medical image analysis", Artificial Intelligence in Medicine, 49, 2010, pp. 117-125.*

(Continued)

*Primary Examiner* — Katherine Fernandez
*Assistant Examiner* — Marjan Saboktakin
(74) *Attorney, Agent, or Firm* — GE Global Patent Operation; Pabitra Chakrabarti (57) ABSTRACT

A method is provided for detecting lesions in ultrasound images. The method includes acquiring ultrasound information, determining discriminative descriptors that describe the texture of a candidate lesion region, and classifying each of the discriminative descriptors as one of a top boundary pixel, a lesion interior pixel, a lower boundary pixel, or a normal tissue pixel. The method also includes determining a pattern of transitions between the classified discriminative descriptors, and classifying the candidate lesion region as a lesion or normal tissue based on the pattern of transitions between the classified discriminative descriptors.

16 Claims, 10 Drawing Sheets

(56) References Cited

U.S. PATENT DOCUMENTS

| | | | |
|---|---|---|---|
| 2005/0234570 A1* | 10/2005 | Horsch | G06F 19/321 |
| | | | 700/93 |
| 2006/0247525 A1 | 11/2006 | Huo et al. | |
| 2008/0069421 A1* | 3/2008 | Abramov | G06K 9/48 |
| | | | 382/132 |
| 2009/0082637 A1 | 3/2009 | Galperin | |
| 2010/0158332 A1 | 6/2010 | Rico et al. | |
| 2011/0026798 A1* | 2/2011 | Madabhushi | G01R 33/56 |
| | | | 382/131 |
| 2012/0014578 A1 | 1/2012 | Karssemeijer et al. | |
| 2013/0023767 A1 | 1/2013 | Mammone | |

OTHER PUBLICATIONS

Yang et al. Content-based retrieval of focal liver lesions using bag of visual words represntations of single and multiphase contrast enhanced CT images, J. Digit. Imaging. (Jun. 2012), 25, pp. 708-719.*

Lu et al. "Classification of summarized videos using hidden markov models on compressed chromaticity signatures", Proceedings of the ninth ACM international conference on multimedia. ACM, 2001.*

Cheng et al. "A novel fuzzy logic approach to mammogram contrast enhancement", Information Sciences, vol. 148, Issues 1-4, Dec. 2002, pp. 167-184.*

Cheng et al., "Automated Breast Cancer Detection and Classification Using Ultrasound Images: A Survey", Pattern Recognition, vol. No. 43, issue No. 1, pp. 299-317, Jan. 2010.

"Computer Aided Diagnosis of Breast Cancer in Automated 3D Breast Ultrasound Using Texture Feature", UMC St Radboud, Radiology Research, pp. 2, 2012.

* cited by examiner

FIG. 12 ations.
METHOD AND SYSTEM FOR LESION DETECTION IN ULTRASOUND IMAGES

BACKGROUND

Breast cancer is one of the leading causes of cancer related deaths in women across the world. Early detection of breast cancer plays an important role in reducing the cancer related deaths. Recently, the use of ultrasound imaging as a breast cancer screening tool has increased considerably, especially in developing countries. In addition to being relatively inexpensive and safe, using ultrasound images as an adjunct screening tool may provide improved detection sensitivity, especially for young women with relatively dense breast tissue.

But, known methods for detecting lesions in ultrasound images of the breast are not without disadvantages. For example, scanning the patient with the ultrasound probe is highly operator dependent, which may result in inconsistent and/or inaccurate ultrasound scans. Moreover, the relatively low quality of ultrasound images and the addition of artifacts such as speckle noise, shadows, ringing, and/or the like may increase the difficulty of lesion detection within ultrasound images. Known methods for detecting lesions in ultrasound images of the breast may also do a relatively poor job of accounting for the significant variations in the shape, size, echogenicity, and margin characteristics of breast lesions.

BRIEF DESCRIPTION

In an embodiment, a method is provided for detecting lesions in ultrasound images. The method includes acquiring ultrasound information, determining discriminative descriptors that describe the texture of a candidate lesion region, and classifying each of the discriminative descriptors as one of a top boundary pixel, a lesion interior pixel, a lower boundary pixel, or a normal tissue pixel. The method also includes determining a pattern of transitions between the classified discriminative descriptors, and classifying the candidate lesion region as a lesion or normal tissue based on the pattern of transitions between the classified discriminative descriptors.

In an embodiment, an ultrasound system includes an ultrasound transducer for transmitting and receiving ultrasound signals to and from an area of interest, a receiver for receiving the ultrasound signals, and a processor coupled to the ultrasound probe. The processor is programmed to acquire ultrasound information, determine discriminative descriptors that describe the texture of a candidate lesion region, and classify each of the discriminative descriptors as one of a top boundary pixel, a lesion interior pixel, a lower boundary pixel, or a normal tissue pixel. The processor is also configured to determine a pattern of transitions between the classified discriminative descriptors, and classify the candidate lesion region as a lesion or normal tissue based on the pattern of transitions between the classified discriminative descriptors.

In an embodiment, a method is provided for detecting lesions in ultrasound images. The method includes acquiring ultrasound information, determining discriminative descriptors that describe the texture of a candidate lesion region, and classifying each of the discriminative descriptors as one of a left boundary pixel, a lesion interior pixel, a right boundary pixel, or a normal tissue pixel. The method also includes determining a pattern of transitions between the classified discriminative descriptors, and classifying the candidate lesion region as a lesion or normal tissue based on the pattern of transitions between the classified discriminative descriptors.

DETAILED DESCRIPTION

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and/or the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide ultrasound systems and methods for detecting lesions in ultrasound images. The method includes acquiring ultrasound information, determining discriminative descriptors that describe the texture of a candidate lesion region, and classifying each of the discriminative descriptors as one of a top boundary pixel, a lesion interior pixel, a lower boundary pixel, or a normal tissue pixel. The method also includes determining a pattern of transitions between the classified discriminative descriptors, and classifying the candidate lesion region as a lesion or normal tissue based on the pattern of transitions between the classified discriminative descriptors.

The systems and methods described and/or illustrated herein may provide automatic lesion/cancer detection in ultrasound images. For example, the systems and methods described and/or illustrated herein may provide automatic detection of lesions in whole breast ultrasound images. A technical effect of at least some embodiments is automatic detection of lesions in ultrasound images. A technical effect of at least some embodiments is that the methods described herein are relatively fast as compared to at least some known lesion detections methods. A technical effect of at least some embodiments is the ability to detect lesions of different sizes and/or shapes. A technical effect of at least some embodiments is a relatively fast and efficient approach for detecting lesions that is able to handle the relatively large amount of data in three-dimensional (3D) images (e.g., 3D ultrasound images of the breast). A technical effect of at least some embodiments is the ability to account for the relatively significant variations in the shape, size, echogenicity, and margin characteristics of lesions.

Figure 1:
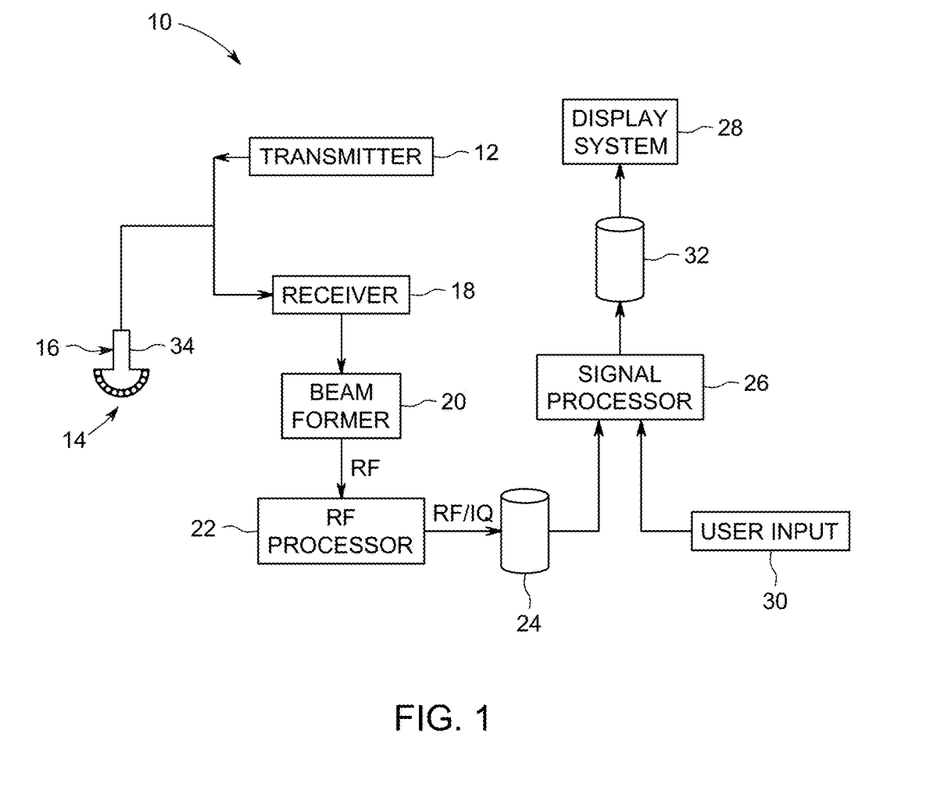
FIG. 1 is a block diagram of an ultrasound system in which various embodiments may be implemented.

FIG. 1 is a block diagram of an ultrasound system 10 in which various embodiments may be implemented. The ultrasound system 10 may be used, for example, to acquire ultrasound data and generate ultrasound images. The ultrasound system 10 includes a transmitter 12 that drives an array of acoustic elements 14 within or formed as part of an ultrasound transducer 16 to emit pulsed ultrasonic signals into a body or other volume. The ultrasonic signals are back-scattered from density interfaces and/or structures in the body or other volume (e.g., blood cells, fatty tissue, and/or muscular tissue in a body) to produce echoes that return to the acoustic elements 14. The echoes are received by a receiver 18. The received echoes are passed through beamforming electronics 20, which performs beamforming and outputs an RF signal. The RF signal then passes through an RF processor 22. The RF processor 22 may include a complex demodulator (not shown) that demodulates the RF signal to form IQ data pairs representative of the echo signals. The RF or IQ signal data may then be routed directly to a memory 24 for storage (e.g., temporary storage).

The ultrasound system 10 also includes a signal processor 26 to process the acquired ultrasound information (e.g., RF signal data or IQ data pairs) and prepare frames of ultrasound information for display on a display system 28. The signal processor 26 is adapted to perform one or more processing operations according to a plurality of selectable ultrasound modalities on the acquired ultrasound information. Acquired ultrasound information may be processed and/or displayed in real-time during a scanning session as the echo signals are received. Additionally or alternatively, the ultrasound information may be stored temporarily in the memory 24 during a scanning session and then processed and/or displayed in less than real-time in a live or off-line operation.

The signal processor 26 is connected to a user input device 30 that may control operation of the ultrasound system 10. The user input device 30 may be any suitable device and/or user interface for receiving user inputs to control, for example, the type of scan or type of transducer to be used in a scan. The display system 28 includes one or more monitors that present patient information, including diagnostic ultrasound images to the user for diagnosis and/or analysis. The ultrasound system 10 may include a memory 32 for storing processed frames of acquired ultrasound information that are not scheduled to be displayed immediately. One or both of the memory 24 and the memory 32 may store 3D data sets of the ultrasound data, where such 3D datasets are accessed to present two-dimensional (2D) and/or 3D images. Multiple consecutive 3D datasets may also be acquired and stored over time, such as to provide real-time 3D or 4D display. The images may be modified and/or the display settings of the display system 28 may be manually adjusted using the user input device 30.

In addition to the acoustic elements 12, various other components of the ultrasound system 10 may be considered to be a component of the ultrasound transducer 16. For example, the transmitter 12, the receiver 18, and/or the beamforming electronics 20 may each be a component of the ultrasound transducer 16. In some embodiments, two or more components of the ultrasound system 10 are integrated into an integrated circuit, which may be a component of the ultrasound transducer 16. For example, the transmitter 12, the receiver 18, and/or the beamforming electronics 20 may be integrated into an integrated circuit.

The ultrasound system 10 may include an ultrasound probe 34 that holds one or more various components of the ultrasound transducer 16. For example, as shown in FIG. 1, the ultrasound probe 34 holds the array of acoustic elements 12. In addition to the acoustic elements 12, and for example, the ultrasound probe 34 may hold the transmitter 12, the receiver 18, the beamforming electronics 20, and/or one or more integrated circuits that include any of the components 12, 18, and/or 20.

Figure 10:
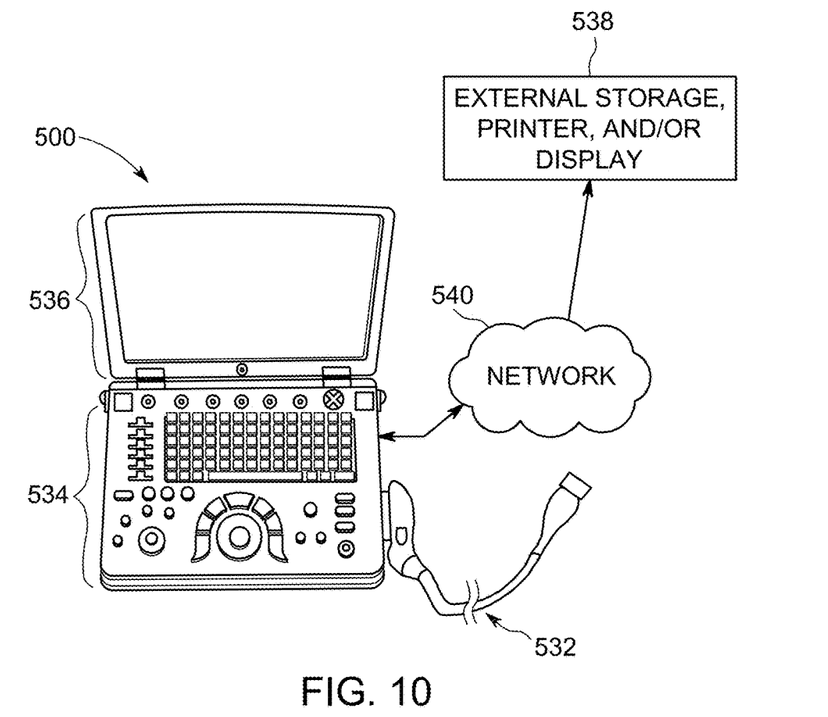
FIG. 10 is a diagram illustrating a three-dimensional (3D) capable miniaturized ultrasound system in which various embodiments may be implemented.
Figure 11:
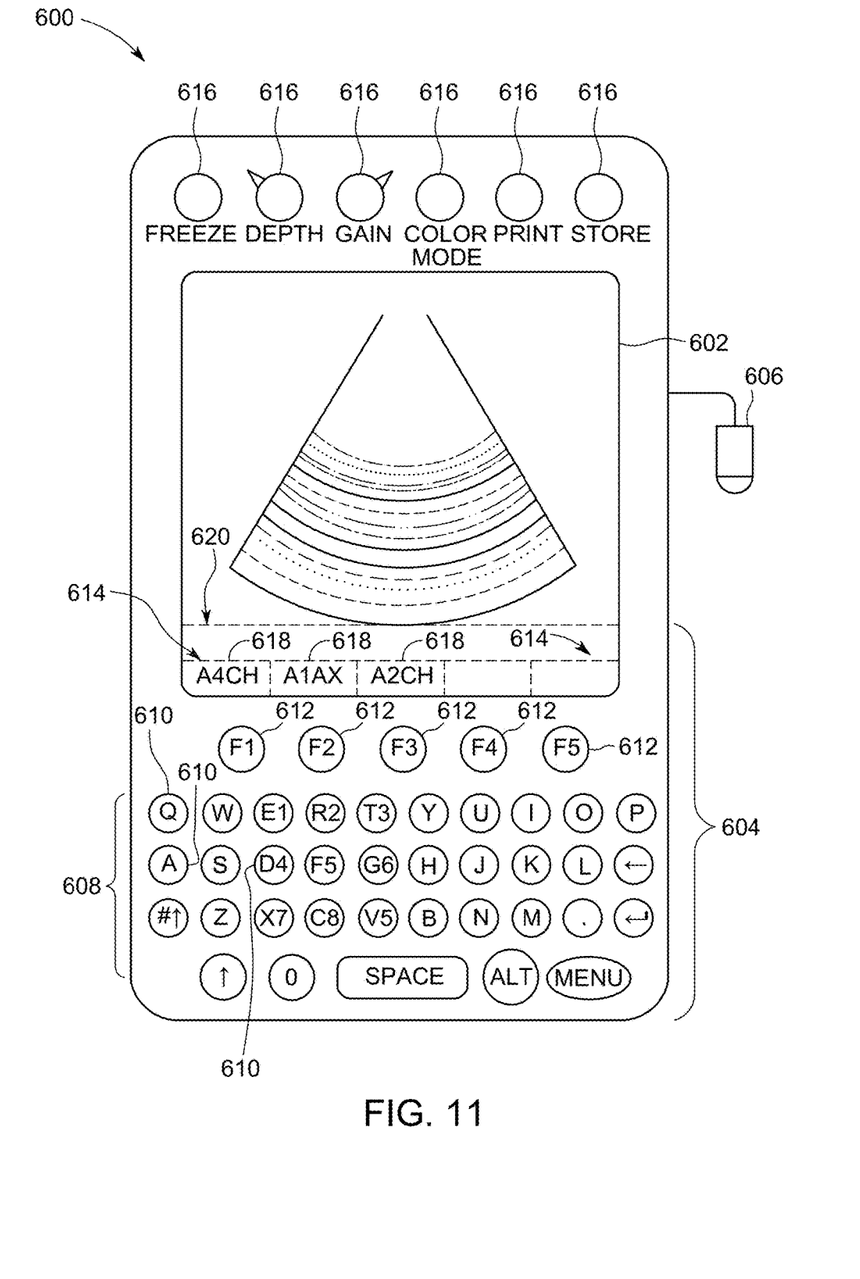
FIG. 11 is a diagram illustrating a 3D capable hand carried or pocket-sized ultrasound imaging system in which various embodiments may be implemented.
Figure 12:
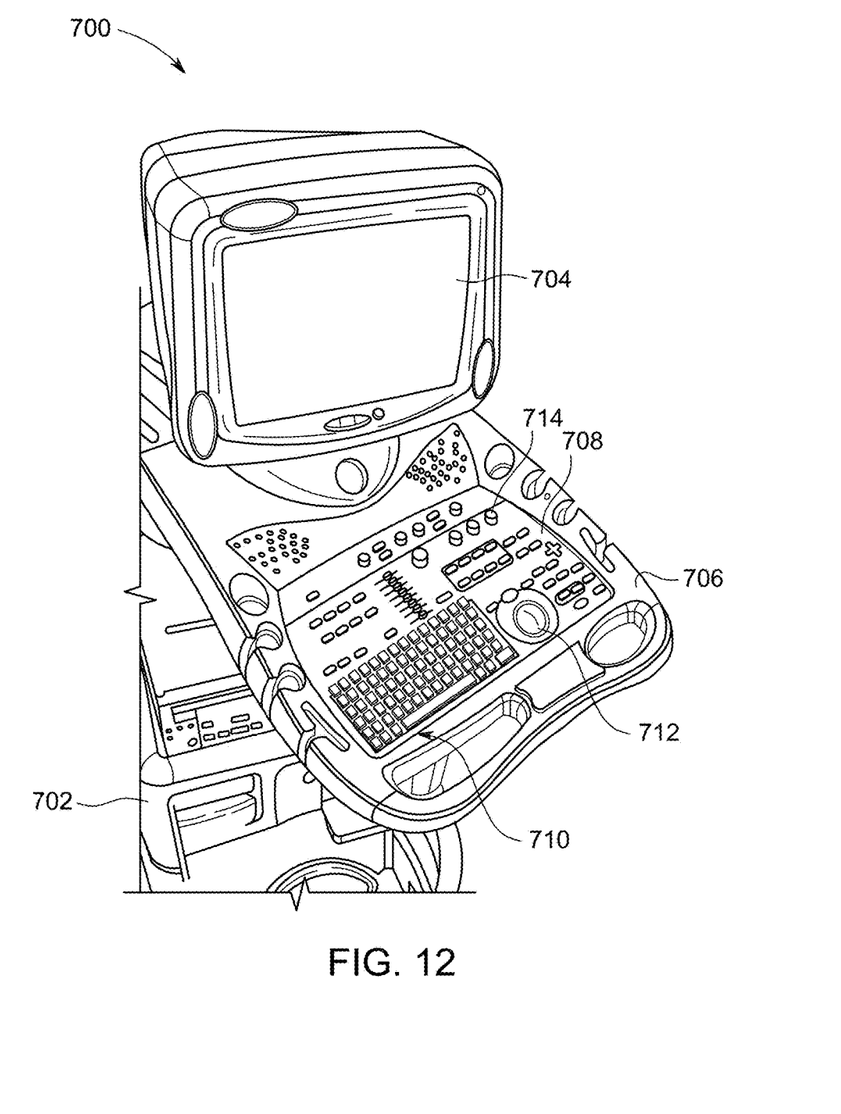
FIG. 12 is a diagram illustrating a 3D capable console type ultrasound imaging system in which various embodiments may be implemented.

The ultrasound system 10 may be embodied in a small-sized system, such as, but not limited to, a laptop computer or pocket sized system as well as in a larger console-type system. FIGS. 10 and 11 illustrate small-sized systems, while FIG. 12 illustrates a larger system.

It should be appreciated that although the system 10 is illustrated as a single modality (i.e., ultrasound) imaging system, the various embodiments may be implemented in or with multi-modality imaging systems. For example, the ultrasound system 10 may be combined with different types of medical imaging systems, such as, but not limited to, a Computed Tomography (CT) system, a Positron Emission Tomography (PET) system, a Single Photon Emission Computed Tomography (SPECT) system, a Magnetic Resonance Imaging (MRI) system, and/or any other system capable of generating images.

Figure 2:
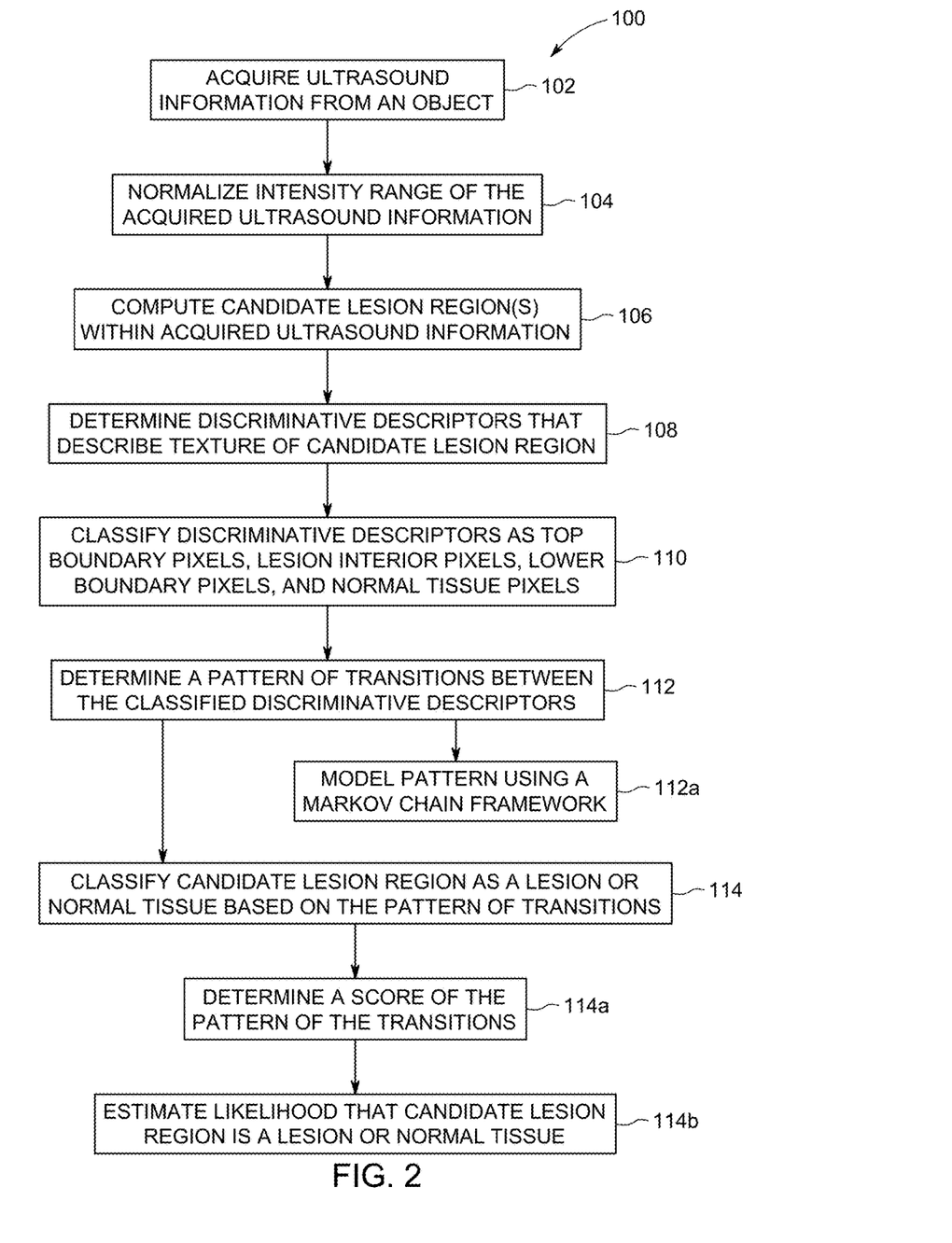
FIG. 2 is a flowchart illustrating a method for detecting lesions in ultrasound images in accordance with various embodiments.

FIG. 2 is a flowchart of a method 100 for detecting lesions in ultrasound images in accordance with various embodiments. It should be noted that although the method 100 is described in connection with ultrasound imaging having particular characteristics, the various embodiments are not limited to ultrasound imaging, nor to any particular imaging characteristics. Rather, the method 100 may be practiced with any imaging modality or any combination of different imaging modalities, such as, but not limited to, CT, PET, SPECT, MRI, and/or the like. For example, the method 100 may be used to detect lesions in other types of images (e.g., CT images, PET images, SPECT images, and/or the like) in addition or alternative to ultrasound images. The method 100 may be particularly meaningful for ultrasound images as the method 100 is configured to consider echoes present at tissue boundaries. The method 100 may be performed, in whole or part, by any suitable imaging system, such as, but not limited to, the ultrasound system 10 (shown in FIG. 1), the ultrasound system 500 (shown in FIG. 10), the ultrasound system 600 (shown in FIG. 11), and/or the ultrasound system 700 (shown in FIG. 12).

At 102, ultrasound information is acquired from an object. For example, the object may constitute a human breast and the method 100 may be performed for detecting a lesion in the breast to thereby detect breast cancer. But, the object for which the ultrasound information is acquired at 102 is not limited to being a human breast. Rather, the object for which the ultrasound information is acquired at 102 may be any other body part (e.g., organ, tissue, and/or fluid) in a human or other animal, such as, but not limited to, a liver, a bladder, a colon, and/or the like. It should be understood that the method 100 may be used to detect a lesion in any body part of a human or other animal, for example for detecting liver cancer, bladder cancer, colon cancer, and/or the like. The ultrasound information acquired at 102 may include 2D and/or 3D information.

The method 100 optionally includes one or more pre-processing steps on the ultrasound information acquired at 102. For example, at 104, the method 100 optionally includes normalizing an intensity range of the ultrasound information acquired at 102, for example using fuzzy logic. Specifically, a fuzzy logic approach is used to map the input image to a fuzzy domain to normalize the intensity range. The fuzzification process at 104 may reduce noise by removing background pixels and noise pixels and/or may enhance the contrast of a lesion by maximizing the fuzzy set entropy.

At 106, the pre-processing step(s) of the method 100 optionally include computing one or more candidate lesion regions within the ultrasound information acquired at 102. Each candidate lesion region is a region (i.e., a location on the imaged body part) of the acquired ultrasound information where a lesion may be present. The method 100 is used to classify whether or not a lesion is present at the candidate lesion region. The goal of the step 106 is to narrow down the search space and reduce the computation time of the remaining steps 108-114 of the method 100.

The candidate lesion region(s) may be computed at 106 using any suitable method, such as, but not limited to, classical intensity/gradient-based thresholding techniques, using a radial gradient index filter, and/or the like. For example, when intensity/gradient thresholding is used, salient edges are first detected with the assumption that the speckle noise follows a Fisher-tippet distribution. The maximum likelihood estimate of the distribution parameter for image region R is given by the following equation:

$$\sigma^2 = \frac{1}{2} \frac{\int_R e^{2I(x,y)} dxdy}{\int_R dxdy}. \qquad (1)$$

If $J_x(x,y)$ and $J_y(x,y)$ are the horizontal and vertical J-divergence computed using the distribution parameters, the feature map is given by:

$$g(x,y) = \sqrt{(J_x^2 + J_y^2)} \qquad (2).$$

Such a detector may pick up the most salient features and may be robust to speckle. A filtering technique based on the radial gradient index (RGI) is then applied on the feature map using:

$$RGI(x, y) = \frac{1}{\sum_{i=1}^{N} |g_i^{max}|} \sum_{i=1}^{N} \langle g_i^{max}, \hat{u}_i \rangle, \qquad (3)$$

where N is the number of symmetric directions, $g_i^{max}$ is the maximum gradient vector along direction i, and $\hat{u}_i$ is the unit radial vector along direction i. After removing pixels with low RGI values, the remaining pixels are grouped using connected components.

Figure 3:
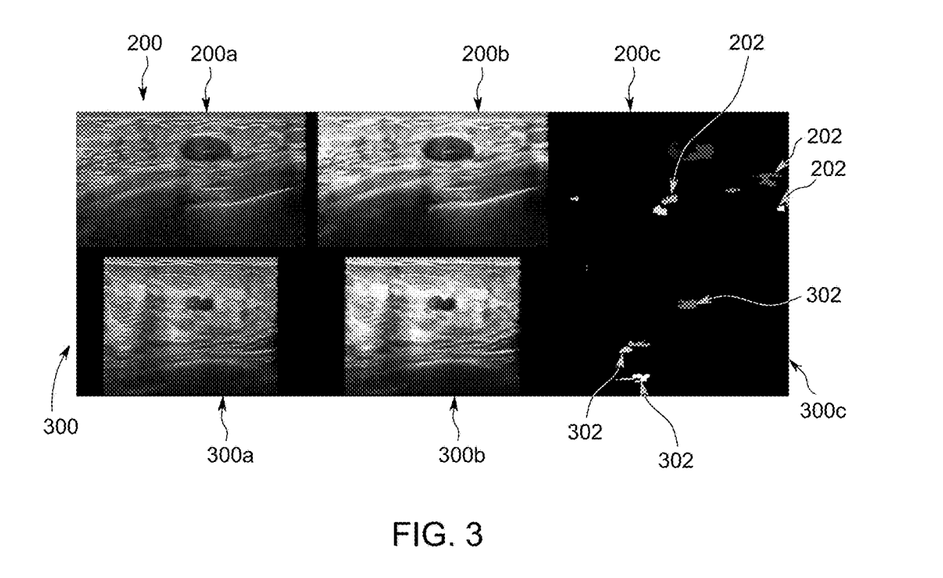
FIG. 3 illustrates two different exemplary ultrasound images that have been acquired and pre-processed according to the method shown in FIG. 2.

FIG. 3 illustrates two different exemplary ultrasound images 200 and 300 that may be acquired at step 102 (shown in FIG. 2) of the method 100 (shown in FIG. 2) and pre-processed according to steps 104 and 106 (shown in FIG. 2) of the method 100. Specifically, FIG. 3 illustrates the ultrasound images 200 and 300 as original images 200*a* and 300*a*, respectively, as acquired at 102 and before being pre-processed at 104 and 106. FIG. 3 also illustrates the ultrasound images 200 and 300 as normalized images 200*b* and 300*b*, respectively, that have been normalized at 104 as described above. Finally, FIG. 3 illustrates the ultrasound images 200 and 300 as respective images 200*c* and 300*c* that include candidate lesion regions 202 and 302, respectively, that have been computed at 106.

Referring again to FIG. 2, after pre-processing the ultrasound information acquired at 102, the method 100 includes determining, at 108, discriminative descriptors that describe the texture of a candidate lesion region (e.g., one or more of the candidate lesion regions 202 and/or 302 shown in the ultrasound images 200*c* and 300*c* of FIG. 3) being analyzed or investigated. A discriminative descriptor may be determined at 108 for any number of the pixels within or around the candidate lesion region. In some embodiments, a descriptor is determined at 108 for each pixel that is within the candidate lesion region.

The discriminative descriptors that are determined at 108 may include any type(s) of discriminative descriptor, such as, but not limited to, a binary-pattern based descriptor, a local binary pattern (LBP) descriptor, a fast retina keypoint (FREAK) descriptor, and/or the like. An LBP descriptor assigns a label to a pixel by thresholding the pixel's neighborhood with the center pixel value. The histogram of the labels can be then used as a texture descriptor. LBP descriptors have been used for medical image analysis and also for classifying masses in ultrasound images of the breast. FREAK descriptors are key-point descriptors inspired by the human visual system. A cascade of binary strings is computed by comparing image intensities over a retinal sampling pattern. The FREAK descriptor is a 64-dimensional descriptor that may be robust to scale, rotation, and/or noise.

Figure 4:
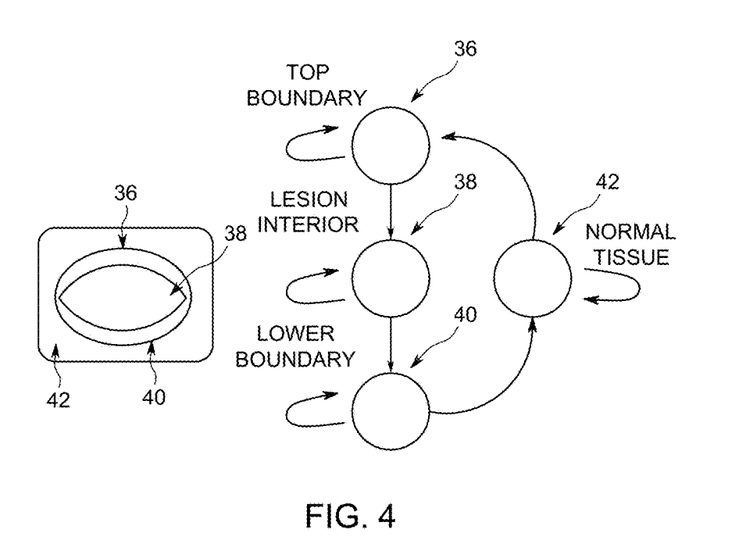
FIG. 4 is a schematic diagram of an exemplary lesion.

Referring to FIG. 4, a lesion may be characterized by the top boundary (i.e., border) 36, interior lesion region 38, and lower boundary (i.e., border) 40 surrounded by normal tissue 42. Accordingly, and referring again to FIG. 1, the method 100 includes classifying, at 110, each of the discriminative descriptors as one of a top boundary pixel, a lesion interior pixel, a lower boundary pixel, or a normal tissue pixel. Any type of classifier may be used to classify at 110 the discriminative descriptors. The classifier(ers) used to classify at 110 the discriminative descriptors may be determined from and/or based on (i.e., learned) using previously annotated training data. Optionally, classifying at 110 each of the descriptors as a top boundary pixel, a lesion interior pixel, a lower boundary pixel, or a normal tissue pixel is performed using a multi-class classifier, such as, but not limited to, a large margin nearest neighbor (LMNN) classifier and/or the like. Moreover, in addition or alternative to classifying, at 110, each of the discriminative descriptors as one of a top boundary pixel, a lesion interior pixel, a lower boundary pixel, or a normal tissue pixel, the classifying step 110 may include classifying each of the discriminative descriptors as one of a left boundary pixel, a lesion interior pixel, a right boundary pixel, or a normal tissue pixel. The classifying step 110 may additionally or alternatively include other patterns of pixels.

In embodiments wherein an LMNN classifier is used, the LMNN classifier is used to determined (i.e., learned) a Mahalanobis distance metric for k-nearest neighbor (kNN) classification by semidefinite programming. The metric is determined with the goal that the k-nearest neighbors always belong to the same class while examples from different classes are separated by a relatively large margin. In an embodiment, a training set $\{y_i, x_i, i=1\}^n$ ($1^n$ of n labeled examples is denoted with inputs $x_i \in R^d$ and class labels $y_i \in \{0,1\}$. The goal is to learn a linear transformation L: $R^d \rightarrow R^d$ that optimizes the kNN classification when distances are measured using the following:

$$D(x_i, x_j) = \|L(x_i - x_j)\|^2 \qquad (4).$$

For each input, i.e., k target neighbors, data with the same label $y_i$ that is desired to have minimal distance to $x_i$ also needs to be specified. The cost function penalizes large distances between each input and its target neighbors, and also penalizes small distances between each input and all other inputs with different labels. The framework may extend relatively seamlessly for multi-class classification.

Figure 5:
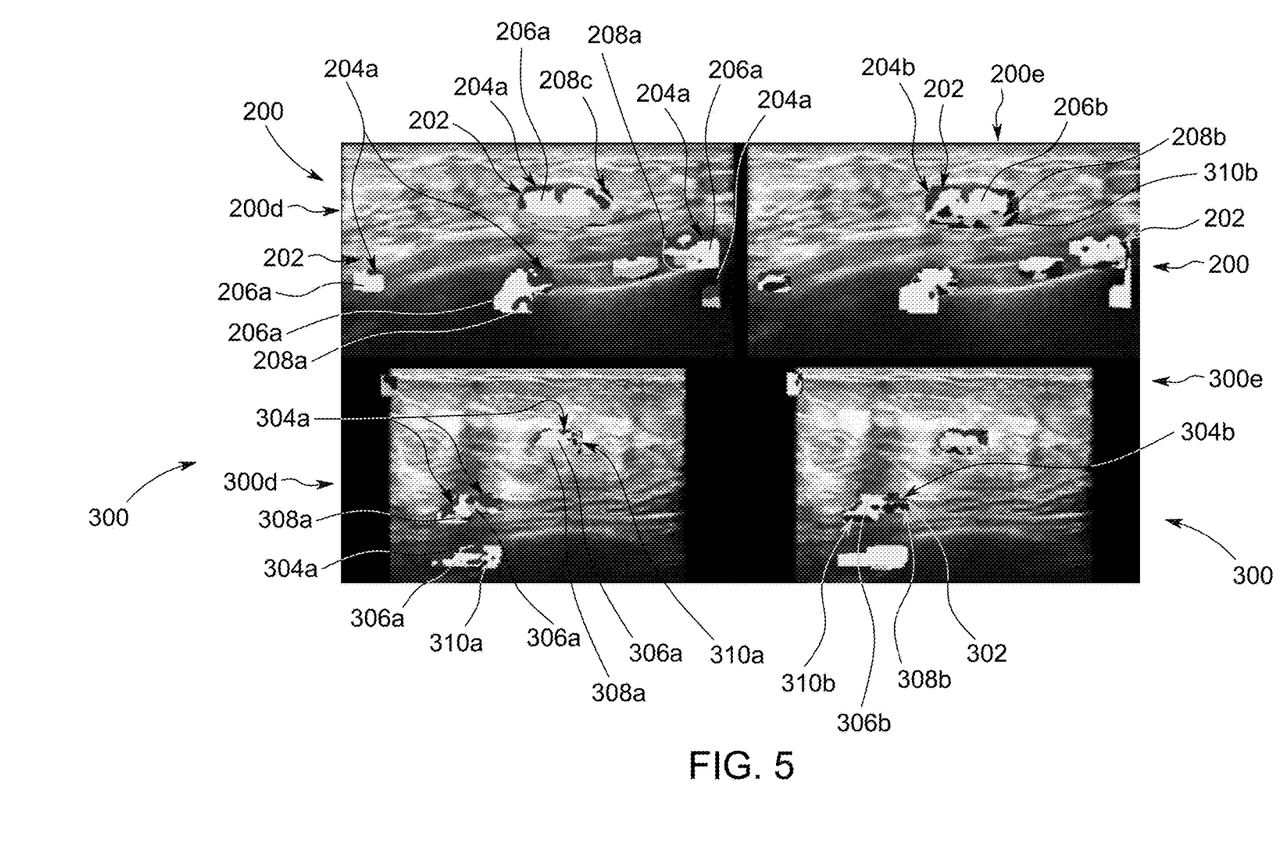
FIG. 5 illustrates the ultrasound images shown in FIG. 3 after the images have been further processed according to the method shown in FIG. 2.

FIG. 5 illustrates an example of the exemplary ultrasound images 200 and 300 shown in FIG. 3 after the discriminative descriptors have been classified at 110 for a plurality of candidate lesion regions 202 and 302. Specifically, FIG. 5 illustrates the ultrasound images 200 and 300 as ultrasound images 200d and 300d, respectively, that represent the ultrasound images 200 and 300, respectively, after the discriminative descriptors have been determined at 108 (shown in FIG. 2) using a FREAK descriptor and classified at 110 using a 4-class LMNN classification for k=3. The discriminative descriptors that have been classified at 110 (shown in FIG. 2) as top boundary pixels are indicated with the shading 204a and 304a, respectively, while the discriminative descriptors that have been classified at 110 as lesion interior pixels are indicated with the shading 206a and 306a, respectively. The discriminative descriptors that have been classified at 110 as lower boundary pixels are indicated with the shading 208a and 308a, respectively, while the discriminative descriptors that have been classified at 110 as normal tissue pixels are indicated with the shading 210a and 310a, respectively. In addition or alternative to the shading, the different classifications of the discriminative descriptors may be differentiated using color, hatching, and/or the like.

FIG. 5 also illustrates the ultrasound images 200 and 300 as ultrasound images 200e and 300e, respectively, that represent the ultrasound images 200 and 300, respectively, after the discriminative descriptors have been determined at 108 using an LBP descriptor and classified at 110 using a 4-class LMNN classification for k=3. The discriminative descriptors that have been classified at 110 as top boundary pixels are indicated with the shading 204b and 304b, respectively, while the discriminative descriptors that have been classified at 110 as lesion interior pixels are indicated with the shading 206b and 306b, respectively. The discriminative descriptors that have been classified at 110 as lower boundary pixels are indicated with the shading 208b and 308b, respectively, while the discriminative descriptors that have been classified at 110 as normal tissue pixels are indicated with the shading 210b and 310b, respectively. In addition or alternative to the shading, the different classifications of the discriminative descriptors may be differentiated using color, hatching, and/or the like.

Figure 6:
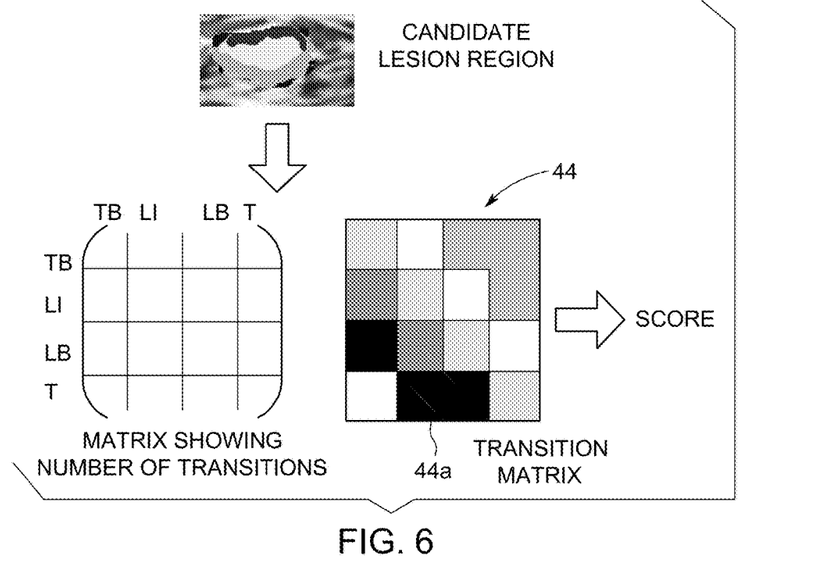
FIG. 6 is a schematic diagram that illustrates an exemplary determination of a pattern of transitions between classified discriminative descriptors that can be used to classify a candidate lesion region as a lesion or normal tissue.

Referring again to FIG. 2, the presence of a lesion within a candidate lesion region gives rise to a specific pattern of boundary pixels (i.e., border pixels), lesion pixels, and normal tissue pixels. In other words, the discriminative descriptors of a lesion are expected to transition between each other in particular fashion. For example, FIG. 4 illustrates an exemplary pattern of boundary pixels (i.e., border pixels) 36 and 40, lesion pixels 38, and normal tissue pixels 42 for a region that includes a lesion. FIG. 6 also illustrates an example of a specific pattern of transitions between discriminative descriptors that have been classified at 110. The pattern of the discriminative descriptors classified at 110 (i.e., the pattern of the top boundary pixels, the lesion interior pixels, the lower boundary pixels, and the normal tissue pixels of the candidate lesion region) can thus be used to estimate the likelihood that the candidate lesion region is a lesion or normal tissue. For example, the pattern of the discriminative descriptors classified at 110 can be compared to a known lesion pattern (e.g., the pattern shown in FIG. 4) to estimate the likelihood that the candidate lesion region is a lesion or normal tissue.

Accordingly, at 112, the method 100 includes determining a pattern of transitions between the discriminative descriptors that have been classified at 110. The pattern of transitions may be determined at 112 using any technique, framework, and/or the like. In some embodiments, the pattern of transitions is determined at 112 by modeling at 112a the pattern of transitions using a Markov chain framework, which may include generating a transition probability matrix that captures expected transitions between the classified discriminative descriptors. For example, the pixel labels (i.e., classified discriminative descriptors) in a region that includes a lesion may be expected to transition in a particular fashion that depends only on the current label, making the transitions Markovian. In this context, the Markov chain models the state of the system (i.e., the discriminative descriptors classified at 110) with a random variable that changes from the top to the bottom of the candidate lesion region. A Markov chain is characterized by a transition probability matrix (TM) that captures the expected transitions between different states. Any number of states may be used. In the exemplary embodiment, the number of states is four. The entries of the $TAL_{4 \times 4}$ is given by:

$$p_{ij} = Pr(X_{n+1} = j | X_n = i); \; i,j \in \{1, \ldots, 4\} \qquad (5),$$

With $\Sigma_j p_{ij} = 1$, where $p_{ij}$ is the probability of the state transitioning from state i at instant n to state j at instant n+1. The TM is estimated from the training data. In other words, the TM is determined (i.e., learned) by observing the transitions on a set of labeled lesions. The state transitions observed in a candidate lesion region is a sample from the chain $x^k = x_1$, $x_2, \ldots, x_k$, with probability in terms of the transition probabilities given by:

$$Pr(x^k) = p_{x_1} \prod_{n=2}^{k} p_{x_{n-1}x_n} = p_{x_1} \prod_{i=1}^{4} \prod_{j=1}^{4} p_{ij}^{n_{ij}}, \quad (6)$$

where $n_{ij}$ denotes the number of times state i is followed by state j.

At 114, the method 100 includes classifying a candidate lesion region as a lesion or normal tissue based on the pattern of transitions between the classified discriminative descriptors determined at 112. For example, the candidate lesion region may be classified as a lesion or normal tissue at 114 by estimating the likelihood that the candidate lesion region is a lesion or normal tissue based on the pattern of transitions determined at 112. Estimating the likelihood that the candidate lesion region is a lesion or normal tissue based on the pattern of transitions determined at 112 may include comparing the pattern of transitions determined at 112 to an expected and/or known lesion pattern. Moreover, estimating the likelihood that the candidate lesion region is a lesion or normal tissue based on the pattern of transitions determined at 112 may include scoring the pattern of transitions determined at 112, for example based on a comparison of the pattern of transitions with an expected transition pattern or a known transition pattern of a lesion.

For example, classifying at 114 the candidate lesion region as a lesion or normal tissue may include determining at 114a a score of the pattern of transitions based on a comparison of the pattern of transitions with an expected and/or a known transition pattern of a lesion. If the pattern of transitions determined at 112 is similar to what is expected and/or known in the presence of a lesion, the candidate lesion region gets a higher score as compared to if the pattern of transitions determined at 112 is less of a match with the expected and/or known pattern of transitions. Based on the score determined at 114a, classifying at 114 the candidate lesion region as a lesion or normal tissue includes estimating at 114b the likelihood that the candidate lesion region is a lesion or normal tissue. In other words, a candidate lesion region may be classified at 114 as a lesion or normal tissue based on the score determined at 114a from the pattern of transitions determined at 112. FIG. 6 is a schematic diagram that illustrates an exemplary determination at 112 (shown in FIG. 2) of an exemplary pattern of transitions 44 between the classified discriminative descriptors that can be used to classify at 114 (shown in FIG. 2) the candidate lesion region as a lesion or normal tissue. For example, FIG. 6 illustrates the creation of an exemplary transition matrix 44a.

Figure 7:
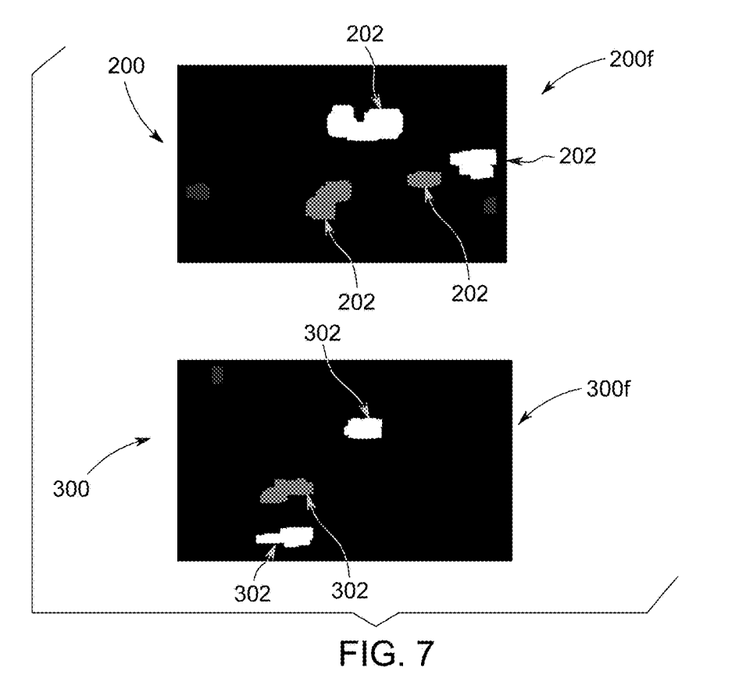
FIG. 7 illustrates the ultrasound images shown in FIGS. 3 and 5 after candidate lesion regions have been classified as lesions or normal tissue according to the method shown in FIG. 2.

FIG. 7 illustrates the exemplary ultrasound images 200 and 300 as ultrasound images 200f and 300f, respectively, that represent the ultrasound images 200 and 300 after the respective candidate lesion regions 202 and 302 have been classified as lesions or normal tissue according to the method 100 (shown in FIG. 2). Specifically, the candidate lesion regions 202 of the ultrasound image 200f have been scored at step 114a (shown in FIG. 2) of the method 100. Candidate lesion regions 202 that are true lesions receive higher scores than candidate lesion regions 202 that are not true lesions. The likelihood that each candidate lesion region 202 is a lesion or normal tissue has been estimated at 114b based on the determined score. The candidate lesion regions 202 are shaded at different intensities to indicate a higher or lower likelihood of being a lesion. In FIG. 7, a higher intensity indicates a higher likelihood of being a lesion. In addition or alternative to the shading, the likelihood of being a lesion or normal tissue may be differentiated using color, hatching, and/or the like.

The candidate lesion regions 302 of the ultrasound image 300f have also been scored at step 114a of the method 100. Candidate lesion regions 302 that have true lesions receive higher scores than candidate lesion regions 202 that do not include true lesions. The likelihood that each candidate lesion region 302 is a lesion or normal tissue has been estimated at 114b based on the determined score. The candidate lesion regions 302 are shaded at different intensities to indicate a higher or lower likelihood of being a lesion. In FIG. 7, a higher intensity indicates a higher likelihood of being a lesion. In addition or alternative to the shading, the likelihood of being a lesion or normal tissue may be differentiated using color, hatching, and/or the like.

Figure 8:
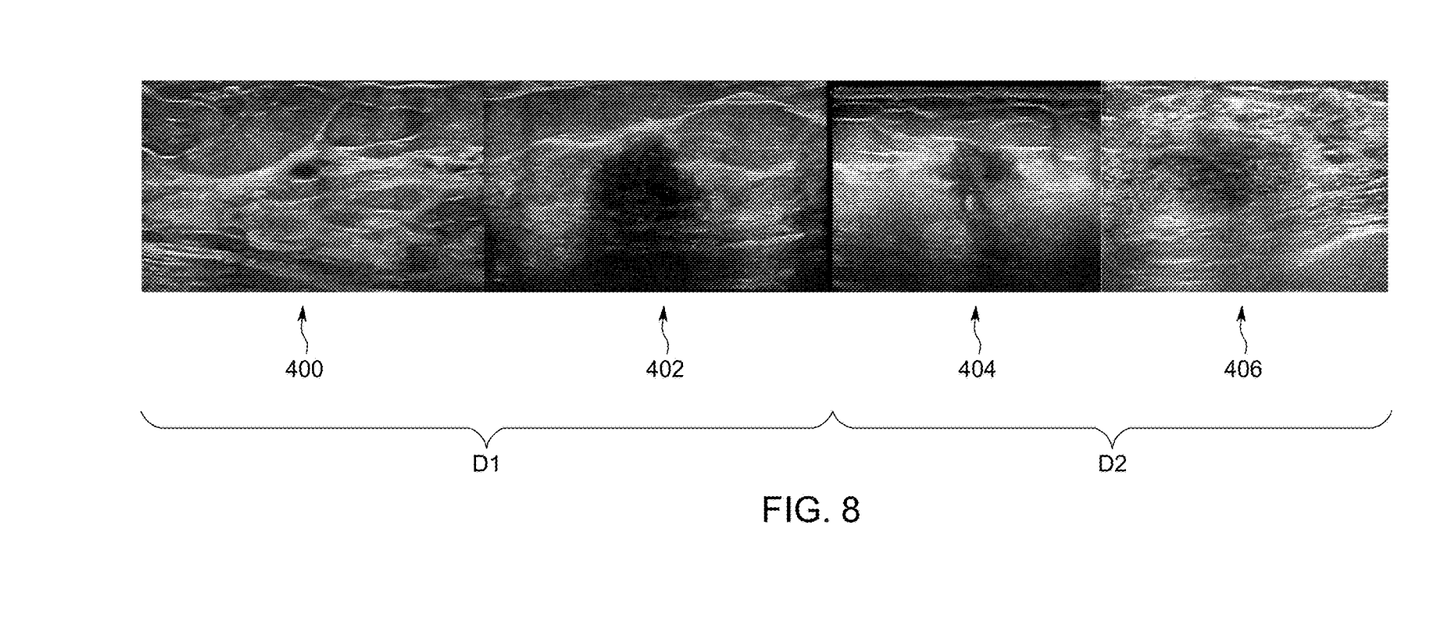
FIG. 8 illustrates exemplary ultrasound images from an experimental evaluation of the method shown in FIG. 2.

Referring now to FIG. 8, the method 100 (shown in FIG. 2) was experimentally evaluated on two different datasets. The first dataset (D1) contained 135 2D images obtained using a GE LOGIQ E9 scanner with a 15 MHz linear probe. The second dataset (D2) contained 159 images obtained using a variety of different scanners, namely LS6 (13 MHz), LOGIC 9 (9 MHz), and Voluson (8 MHz). From the biopsy data, 100 images in D2 contained malignant lesions, 23 contained benign lesions and the remaining images do not contain any lesion. The first dataset D1 contains 139 lesions, and the second dataset D2 contains 148 lesions, the boundaries of which have been manually marked by an experienced radiologist. FIG. 8 illustrates a few images from the datasets D1 and D2. Specifically, FIG. 8 illustrates two exemplary ultrasound images 400 and 402 from the first dataset D1, and two exemplary ultrasound images 404 and 406 from the second dataset D2. FIG. 8 illustrates that the lesions vary significantly in terms of shape, size, intensity, margin characteristics, etc.

The implementation details of the experimental evaluation will now be described. For the FREAK descriptor, default parameters were used, i.e., number of octaves covered by the detected points is set to 4 and the patternScale (scale applied to the pattern used for sampling the neighborhood of a keypoint) is set to 22. For the LBP feature, a 16×16 image block is taken around the keypoint and uniform LBP with eight neighborhood is computed. Three target neighbors are used for LMNN classification. For training, 10 randomly chosen images from the first dataset D1 were used, and 10 data points were manually marked for each of the four classes, thus resulting in a total of 100 examples of each class. There was no overlap between the train and test subjects. The unoptimized Matlab implementation of the algorithm takes around 2 seconds for a 302×504 image for feature computation, pixel classification, and likelihood computation combined.

Figure 9:
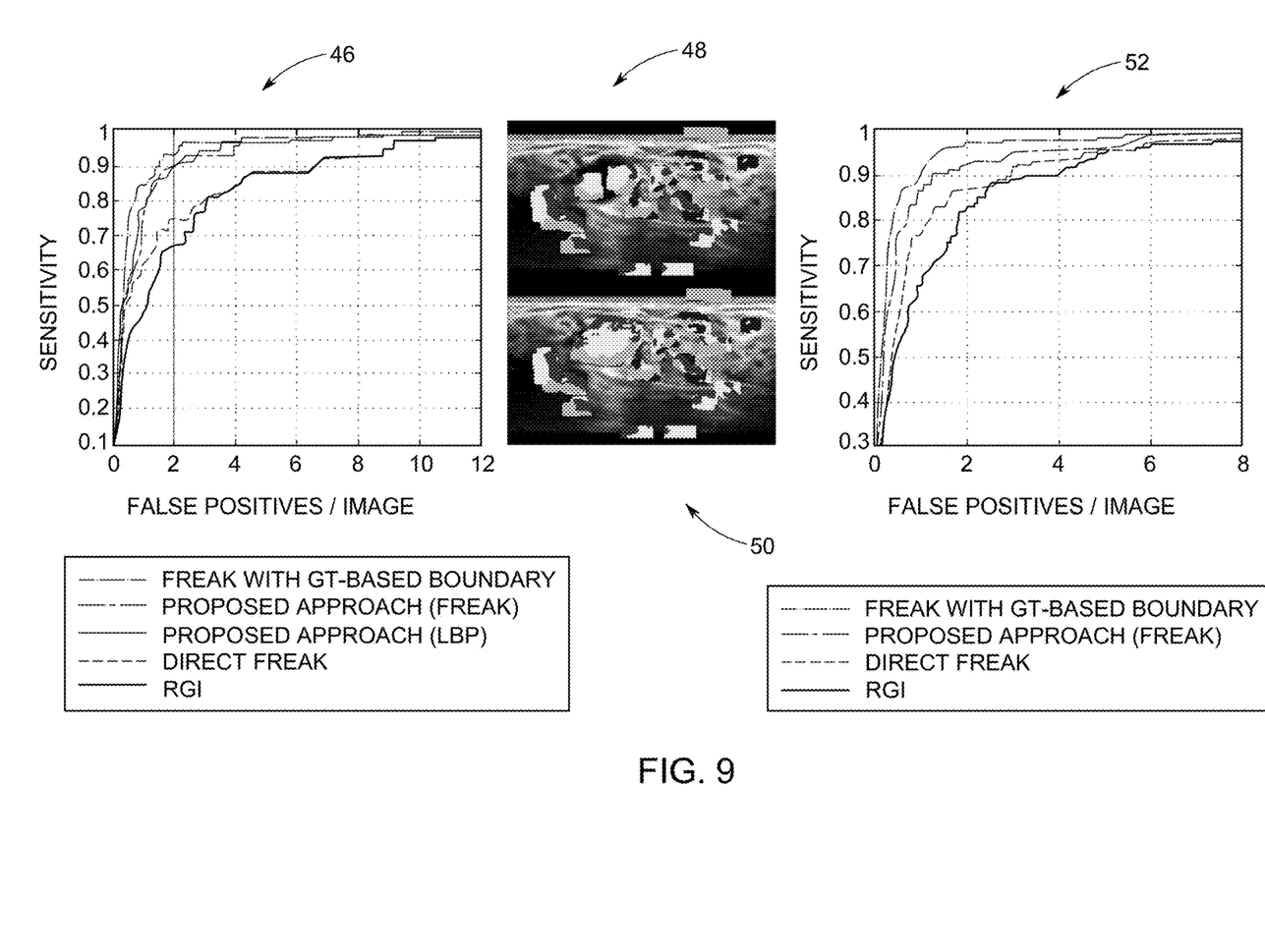
FIG. 9 illustrates the results of the experimental evaluation of the method shown in FIG. 2.

An evaluation of the first dataset D1 of the experimental evaluation will now be described. The performance was tested using a ROC (Receiver Operating Characteristic). A lesion is counted as detected if a bounding box of the lesion marked by the radiologist overlaps with a bounding box given by the method 100. A bounding box defines a boundary of a candidate lesion region wherein a lesion is present within the boundary. The candidate generation step attains a sensitivity of approximately 99% with an average of 12 false detections per image. All the candidate regions generated are passed on to the next stage for feature computation. FIG. 9 shows the results obtained using the method 100. FIG. 9 includes a graph 46 that illustrates the results of using the method 100 on the first dataset D1 with a FREAK descriptor (identified as the "Proposed approach (Freak)" in the graph 46) and the results of using the method 100 on the first dataset D1 with an LBP descriptor (identified as the "Proposed approach (LBP)" in the graph 46). The sensitivity curves of the graph 46 illustrate that the method 100 works relatively well for both the FREAK and LBP descriptors. The ROC for RGI filtering, which is also used for initial lesion detection, is also shown in the graph 46 for comparison. To see how the Markov chain framework affects the performance, an experiment was performed in which the classifier is used to directly classify the descriptors as lesion or non-lesion. The score of a candidate lesion region is given by the number of lesion pixels in that region. The sensitivity curves of the graph 46 of FIG. 9 illustrate that the method 100 (whether using the FREAK descriptor or the LBP descriptor) performs significantly better than the direct approach (referred to as "Direct Freak" in the graph 46). If the candidate lesion regions encompass the whole lesion, then the method 100 can take into account all the tissue transitions as compared to if the candidate lesion region covers only a part of the lesion. To understand how this affects the performance, the candidate lesion region for the true lesion is altered to encompass the whole lesion based on four boundary points marked by a radiologist. All the other candidate lesion regions remain unchanged. Images 48 and 50 of FIG. 9 illustrate the actual (top) and modified (bottom) candidate lesion regions for the first dataset D1 and the second dataset D2, respectively. The sensitivity curves of the graph 46 of FIG. 9 illustrate that though the method 100 may not be overly sensitive, the method 100 may perform better with candidate lesion regions encompassing the whole lesion.

An analysis of the robustness of the method 100 using the second dataset D2 will now be described. To analyze the robustness of the method 100 to varying data acquisition platforms, scanner types, etc., the performance of the method 100 was evaluated on the second dataset D2 without retraining the classifier or changing any other parameters of the algorithm of the method 100. The sensitivity curves of the graph 52 of FIG. 9 illustrate that the performance of the method 100 (identified as the "Proposed approach (Freak)" in the graph 52) and also the performances of the direct Freak approach and the GT-based boundary approach. The sensitivity curves of the graph 52 of FIG. 9 illustrate that the method 100 may work relatively well on completely unseen data, data, possibly without requiring any training, thus signifying that the method 100 may be robust.

FIG. 10 illustrates a 3D-capable miniaturized ultrasound system 500 having an ultrasound transducer 532 that may be configured to acquire 3D ultrasonic data or multi-plane ultrasonic data. For example, the ultrasound transducer 532 may have a 2D array of acoustic elements. A user interface 534 (that may also include an integrated display 536) is provided to receive commands from an operator. As used herein, "miniaturized" means that the ultrasound system 530 is a handheld or hand-carried device or is configured to be carried in a person's hand, pocket, briefcase-sized case, and/or backpack. For example, the ultrasound system 530 may be a hand-carried device having a size of a typical laptop computer. The ultrasound system 530 is easily portable by the operator. The integrated display 536 (e.g., an internal display) is configured to display, for example, one or more medical images.

The ultrasonic data may be sent to an external device 538 via a wired or wireless network 540 (or direct connection, for example, via a serial or parallel cable or USB port). In some embodiments, the external device 538 may be a computer or a workstation having a display, or the DVR of the various embodiments. Alternatively, the external device 538 may be a separate external display or a printer capable of receiving image data from the hand carried ultrasound system 530 and of displaying or printing images that may have greater resolution than the integrated display 536.

FIG. 11 illustrates a hand carried or pocket-sized ultrasound imaging system 600 wherein the display 602 and user interface 604 form a single unit. By way of example, the pocket-sized ultrasound imaging system 600 may be a pocket-sized or hand-sized ultrasound system approximately 2 inches wide, approximately 4 inches in length, and approximately 0.5 inches in depth and weighs less than 3 ounces. The pocket-sized ultrasound imaging system 600 generally includes the display 602, user interface 604, which may or may not include a keyboard-type interface and an input/output (I/O) port for connection to a scanning device, for example, and an ultrasound transducer 606. The display 602 may be, for example, a 320×320 pixel color LCD display (on which a medical image 484 may be displayed). A typewriter-like keyboard 608 of buttons 610 may optionally be included in the user interface 604.

Multi-function controls 612 may each be assigned functions in accordance with the mode of system operation (e.g., displaying different views). Therefore, each of the multi-function controls 612 may be configured to provide a plurality of different actions. Label display areas 614 associated with the multi-function controls 612 may be included as necessary on the display 602. The system 600 may also have additional keys and/or controls 616 for special purpose functions, which may include, but are not limited to "freeze," "depth control," "gain control," "color-mode," "print," and "store."

One or more of the label display areas 614 may include labels 618 to indicate the view being displayed or allow a user to select a different view of the imaged object to display. The selection of different views also may be provided through the associated multi-function control 612. The display 602 may also have a textual display area 620 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 600 and the miniaturized ultrasound system 500 (shown in FIG. 10) may provide the same scanning and processing functionality as the ultrasound system 10 (shown in FIG. 1)

FIG. 12 illustrates an ultrasound imaging system 700 provided on a movable base 702. The portable ultrasound imaging system 700 may also be referred to as a cart-based system. A display 704 and user interface 706 are provided and it should be understood that the display 704 may be separate or separable from the user interface 706. The user interface 706 may optionally be a touchscreen, allowing the operator to select options by touching displayed graphics, icons, and/or the like.

The user interface 706 also includes control buttons 708 that may be used to control the portable ultrasound imaging system 700 as desired or needed, and/or as typically provided. The user interface 706 provides multiple interface options that the user may physically manipulate to interact with ultrasound data and other data that may be displayed, as well as to input information and set and change scanning parameters and viewing angles, etc. For example, a keyboard 710, trackball 712, and/or multi-function controls 714 may be provided.

It should be noted that although the various embodiments may be described in connection with an ultrasound system, the methods and systems are not limited to ultrasound imaging or a particular configuration thereof. The various embodiments of ultrasound imaging may be implemented in combination with different types of imaging systems, for example, multi-modality imaging systems having an ultrasound imaging system and one of an x-ray imaging system, magnetic resonance imaging (MRI) system, computed-tomography (CT) imaging system, positron emission tomography (PET) imaging system, among others. Further, the various embodiments may be implemented in non-medical imaging systems, for example, non-destructive testing systems such as ultrasound weld testing systems or airport baggage scanning systems.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and/or the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for detecting lesions in ultrasound images, said method comprising:
   transmitting ultrasound information by an ultrasound transducer to a region of interest;
   acquiring reflected ultrasound information from the region of interest by an ultrasound transducer into a processor coupled to the ultrasound transducer;
   generating ultrasound images corresponding to the ultrasound information on a display system;
   determining using the processor, discriminative descriptors that describe the texture of a candidate lesion region within the ultrasound images;
   classifying using the processor, each of the discriminative descriptors as one of a top boundary pixel, a lesion interior pixel, a lower boundary pixel, or a normal tissue pixel;
   determining using the processor, a pattern of transitions between the classified discriminative descriptors, wherein the pattern of transitions comprises a transition matrix representing transitions between a plurality of pixels belonging to a lesion's top boundary, a plurality of pixels belonging to the lesion's interior, a plurality of pixels belonging to the lesion's lower boundary, and a plurality of pixels belonging to a normal tissue;

classifying using the processor, the candidate lesion region as a lesion or normal tissue based on the pattern of transitions; and differentiating on the ultrasound images, a likelihood of the candidate lesion region being a lesion or normal tissue determined based on the pattern of transitions, by a respective intensity of at least one of: shade, color and hatching.

2. The method of claim 1, wherein determining using the processor, the discriminative descriptors comprises determining using the processor, a discriminative descriptor for each pixel within the candidate lesion region.

3. The method of claim 1, wherein each discriminative descriptor is at least one of a binary-pattern based descriptor, a local binary pattern (LBP) descriptor, or a fast retina keypoint (FREAK) descriptor.

4. The method of claim 1, wherein classifying using the processor, each of the discriminative descriptors comprises classifying using the processor, the discriminative descriptors using at least one of a multi-class classifier or large margin nearest neighbor (LMNN) classifier.

5. The method of claim 1, wherein determining using the processor, the pattern of transitions comprises modeling using the processor, the pattern of transitions using a Markov chain framework.

6. The method of claim 1, wherein classifying using the processor, the candidate lesion region as a lesion or normal tissue comprises scoring using the processor, the pattern of transitions based on a comparison of the pattern of transitions with at least one of an expected transition pattern or a known transition pattern of a lesion.

7. The method of claim 1, wherein classifying using the processor, the candidate lesion region as a lesion or normal tissue comprises determining using the processor, a score of the pattern of transitions based on a comparison of the pattern of transitions with at least one of an expected transition pattern or a known transition pattern of a lesion, and estimating using the processor, the likelihood that the candidate lesion region is a lesion or normal tissue based on the determined score.

8. The method of claim 1, further comprising computing using the processor, the candidate lesion region using intensity/gradient thresholding.

9. The method of claim 1, further comprising normalizing using the processor, an intensity range of the ultrasound information using fuzzy logic.

10. An ultrasound system comprising:
an ultrasound transmitter for transmitting ultrasound signals to an area of interest;
a receiver for receiving the reflected ultrasound signals from the area of interest; and
a processor coupled to the ultrasound probe, the processor programmed to:
acquire ultrasound information;
determine discriminative descriptors that describe the texture of a candidate lesion region;
classify each of the discriminative descriptors as one of a top boundary pixel, a lesion interior pixel, a lower boundary pixel, or a normal tissue pixel;
determine a pattern of transitions between the classified discriminative descriptors, wherein the pattern of transitions comprises a transition matrix representing transitions between a plurality of pixels belonging to a lesion's top boundary, a plurality of pixels belonging to the lesion's interior, a plurality of pixels belonging to the lesion's lower boundary, and a plurality of pixels belonging to a normal tissue; and
classify the candidate lesion region as a lesion or normal tissue based on the pattern of transitions.

11. The ultrasound system of claim 10, wherein the processor is configured to determine the discriminative descriptors by determining a discriminative descriptor for each pixel within the candidate lesion region.

12. The ultrasound system of claim 10, wherein each discriminative descriptor is at least one of a binary-pattern based descriptor, a local binary pattern (LBP) descriptor, or a fast retina keypoint (FREAK) descriptor.

13. The ultrasound system of claim 10, wherein the processor is configured to classify each of the discriminative descriptors using at least one of a multi-class classifier or large margin nearest neighbor (LMNN) classifier.

14. The ultrasound system of claim 10, wherein the processor is configured to determine the pattern of transitions between the classified discriminative descriptors by modeling the pattern of transitions using a Markov chain framework.

15. The ultrasound system of claim 10, wherein the processor is configured to classify the candidate lesion region as a lesion or normal tissue by scoring the pattern of transitions based on a comparison of the pattern of transitions with at least one of an expected transition pattern or a known transition pattern of a lesion.

16. The ultrasound system of claim 10, wherein the processor is configured to classify the candidate lesion region as a lesion or normal tissue by determining a score of the pattern of transitions based on a comparison of the pattern of transitions with at least one of an expected transition pattern or a known transition pattern of a lesion, and estimating the likelihood that the candidate lesion region is a lesion or normal tissue based on the determined score.

* * * * *